United States Patent [19]

Moriwaki et al.

[11] Patent Number: 5,721,231
[45] Date of Patent: Feb. 24, 1998

[54] THIENOTRIAZOLODIAZEPINE COMPOUND AND PHARMACEUTICAL USE THEREOF

[75] Inventors: Minoru Moriwaki, Osaka; Hiroyuki Kitani; Syuji Ehara, both of Chikujo-gun; Hirotsugu Komatsu; Mariko Amano, both of Iruma, all of Japan

[73] Assignee: Yoshitomi Pharmaceutical Industries, Ltd., Osaka, Japan

[21] Appl. No.: 535,913

[22] Filed: Sep. 28, 1995

Related U.S. Application Data

[63] Continuation-in-part of PCT/JP94/00500, Mar. 28, 1994.

[30] Foreign Application Priority Data

Mar. 30, 1993 [JP] Japan .................................. 5-095398
Aug. 9, 1993 [JP] Japan .................................. 5-218195

[51] Int. Cl.$^6$ ........................ A61K 31/55; C07D 495/14
[52] U.S. Cl. ............................................ 514/220; 540/560
[58] Field of Search ............................ 540/560; 514/220

[56] References Cited

U.S. PATENT DOCUMENTS

| | | | |
|---|---|---|---|
| 4,992,437 | 2/1991 | Naka et al. | 514/220 |
| 5,439,905 | 8/1995 | Naka et al. | 514/220 |

FOREIGN PATENT DOCUMENTS

| | | |
|---|---|---|
| 0 387 613 A1 | 9/1990 | European Pat. Off. . |
| A 0 559 891 A1 | 9/1993 | European Pat. Off. . |
| 0 638 560 A1 | 2/1995 | European Pat. Off. . |
| 0 656 361 A1 | 6/1995 | European Pat. Off. . |
| A 0 661 284 A1 | 7/1995 | European Pat. Off. . |
| 3-223290 | 10/1991 | Japan . |
| 93/07129 | 4/1993 | WIPO . |
| 93/12117 | 6/1993 | WIPO . |
| A 94/05673 | 3/1994 | WIPO . |

OTHER PUBLICATIONS

Derwent Abstract of EP 0 387 613 A1, WPI Acc. No. 90-276391/37.

Harrison's Principles of Internal Medicine, 13th ed. (1994), vol. 2, pp. 1826–1829, Isselbacher et al.

Cecil Textbook of Medicine, 19th ed (1992) Wyngaarden et al, pp. 1049–1053.

*Primary Examiner*—Philip I. Datlow
*Attorney, Agent, or Firm*—Wenderoth, Lind & Ponack

[57] ABSTRACT

N-(4-(4-chlorophenyl)-2,3,9-trimethyl-6H-thieno [3,2-f][1,2,4]triazolo[4,3-a][1,4]diazepin-6-yl )-N'-(2-methoxyphenyl)urea, optical isomers thereof and pharmaceutically acceptable salts thereof. The compounds of the present invention strongly and selectively inhibit the expression of VCAM-1 and have an inhibitory effect on leukocyte adhesion to vascular endothelial cells. Accordingly, the compounds of the present invention can be used as cell adhesion inhibitors for prophylaxis or treatment of various diseases in which cell adhesion is involved in the onset and progress thereof.

12 Claims, No Drawings

THIENOTRIAZOLODIAZEPINE COMPOUND AND PHARMACEUTICAL USE THEREOF

The present application is a continuation-in-part of PCT/JP94/00500, filed Mar. 28, 1994.

FIELD OF THE INVENTION

The present invention relates to a novel thienotriazolodiazepine compound having superior inhibitory effect on cell adhesion, optical isomers thereof, pharmaceutically acceptable salts thereof and pharmaceutical use thereof.

BACKGROUND ART

In various inflammatory and allergic diseases, infiltration of so-called inflammatory cells, leukocytes in a general sense, such as polymorphonuclear leukocytes, macrophages and lymphocytes is directly connected with the symptoms of the diseases. Although the adhesion of leukocytes to vascular endothelial cells has been considered the first step of infiltration of leukocytes, its mechanism has been uncertain. The recent progress in molecular biology has enabled investigators to identify the molecules concerned with adhesion, and their functional significance has been clarified, that is, the phenomenon of adhesion induced by specific binding of the certain adhesion molecules expressed on leukocytes to their ligands on vascular endothelial cells, followed by infiltration of leukocytes into inflammatory sites. While the combinations, as shown in the following Table, of molecules involved in the adhesion of leukocytes to vascular endothelial cells are considered to be particularly important, the degree of involvement of respective adhesion molecules in various inflammatory and allergic diseases is not entirely clear.

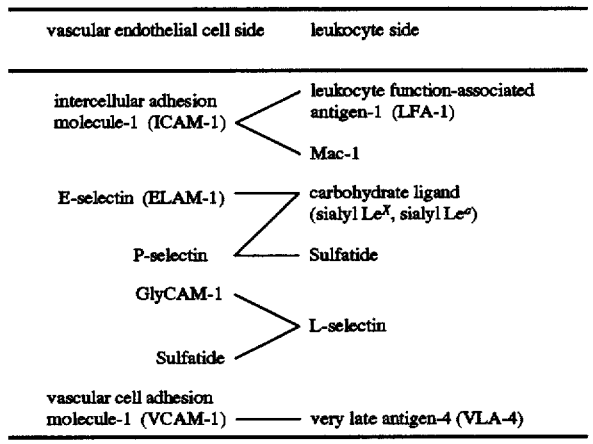

Vascular cell adhesion molecule-1 (VCAM-1) is one of these adhesion molecules. It is expressed mainly on vascular endothelial cells and binds to very late antigen-4 (VLA-4), a ligand which is expressed on the surface of leukocytic cells such as lymphocytes, monocytes/macrophages and eosinophils [S. Montefort et al., Eur. Resp. J. 6, pp 1044–1054 (1993)]. The infiltration of leukocytic cells into the tissues, which is induced by the adhesion via VCAM-1, is considered to play an important role in various inflammatory and allergic diseases. For example, the level of VCAM-1 expression in nasal mucosal tissue and infiltration of eosinophils into the tissue increase upon elicitation by antigen in the patients suffering from allergic rhinitis, thus suggesting the involvement of VCAM-1 in the infiltration of eosinophils into the inflammatory tissues [Bong-Jae Lee et al., J. Allergy Clin. Immunol., 94, 1006–1016 (1994)]. Elevated expression of VCAM-1 in bronchial mucosal tissue is also found in the patients with asthma (T. Fukuda et al., Am. J. Respir. Cell Mol. Biol., in press), which also suggests the involvement of infiltration of eosinophils via VCAM-1 in asthma [S. Montefort et al., Eur. Resp. J. 6, pp 1044–1054 (1993)]. The involvement of VCAM-1 in infiltration of eosinophils has been confirmed with respect to cultured human cells as an in vitro model [R. P. Schleimer et al., J. Immunol., 148, 1086–1092 (1992)] and mice as an in vivo model [H. Nakajima et al., J. Exp. Med., 179, 1145–1154 (1994)]. Investigators have also reported elevated expression of VCAM-1 in dermal tissues, which is caused by antigenic stimulation, in delayed type hypersensitivity response of skin, as well as involvement of VCAM-1 in contact dermatitis [P. Norris et al., J. Invest. Dermatol., 96, 763–770 (1991)]. Moreover, researchers have found elevated expression of VCAM-1 in synovial tissues of the patients suffering from rheumatoid arthritis and osteoarthritis. This in turn, suggests VCAM-1's involvement in the infiltration of VLA-4 positive cells [J. Morales-Ducret, J. Immunol., 149, 1424–1431 (1992)].

As is evident from the various aforementioned reports, VCAM-1 is considered to play an important role in the infiltration of leukocytic cells in various inflammatory and allergic diseases, particularly in the infiltration of leukocytic cells into inflammatory sites. A recent report has revealed involvement of soluble VCAM-1 in angiogenesis [A. E. Koch et al., Nature, 376, 517–519 (1995)]. Angiogenesis is considered to be involved in malignant tumor, particularly the growth and metastasis of solid tumor, diabetes and rheumatoid arthritis, so that VCAM-1 is considered to be one of the important molecules in these diseases.

Therefore it follows that a compound which suppresses the expression of VCAM-1 is effective for the prophylaxis and treatment of rhinitis such as allergic rhinitis and pollinosis, dermatitis such as contact dermatitis and atopic dermatitis, asthmatic diseases including chronic bronchial asthma, inflammatory bowel diseases such as Crohn's disease and ulcerative colitis, nephritis including glomerular nephritis, autoimmune diseases such as rheumatoid arthritis and systemic lupus erythematosus, osteoarthritis, diabetes, malignant tumor, ischemic heart disease and graft rejection after organ transplantation.

Incidentally, intercellular adhesion molecule-1 (ICAM-1) and leukocyte function-associated antigen-1 (LFA-1) are known to be deeply involved in not only cell adhesion, but also cell activation. For example, LFA-1 on T lymphocytes binds to ICAM-1 on macrophages to activate T lymphocytes. Accordingly, a substance which inhibits the binding between ICAM-1 and LFA-1 is expected to show immunosuppressive action.

Furthermore, elevated expression of ICAM-1 and E-selectin in inflammatory sites of inflammatory skin diseases (e.g. contact dermatitis and light eruptions caused by high photosensitivity) and rheumatoid arthritis has been reported, and involvement of ICAM-1 and Mac-1 in asthma has been suggested. It has also been reported that cell adhesion via ICAM-1 plays an important role in graft rejection after organ transplantation, and that adhesion molecules are concerned with tumor metastasis.

It has also been reported that expression of adhesion molecules has been promoted in various animal inflammatory models (e.g. delayed type hypersensitivity model and autoimmune nephritic model) and that anti-ICAM-1 antibody and anti-LFA-1 antibody inhibit inflammatory responses (e.g. adjuvant-induced arthritis and collagen-induced arthritis). Moreover, the role of adhesion molecules in activating eosinophils in monkey asthmatic models has been clarified. Furthermore, the effectiveness of anti-LFA-1 antibody and anti-ICAM-1 antibody in mouse heterotopic heart transplantation models has been reported, suggesting the involvement of adhesion molecules in graft rejection, as in human beings.

Various steroidal agents, non-steroidal antiinflammatory agents, and inhibitors of the release of inflammation- and/or allergy-related mediators have been used as therapeutic agents for various inflammatory and allergic diseases. Of these pharmaceutical agents, steroidal agents often cause severe side-effects and other pharmaceutical agents fail to achieve sufficient therapeutic effects.

Recent studies have increasingly revealed that various cell adhesion molecules are deeply concerned with the onset and progress of some inflammatory and allergic diseases, and a compound having inhibitory action on cell adhesion is expected to be a superior antiinflammatory agent or anti-allergic agent. For example, Proc. Natl. Acad. Sci. U.S.A., vol. 88, pp 355–359 (1991) teaches that N-(fluorenyl-9-methoxycarbonyl)amino acids suppress reactions in various animal models of inflammation by inhibiting adhesion of leukocytes, and an abstract from American Federation for Clinical Research Annual Meeting, May 6, 1991, teaches that the same series of compounds inhibit leukocyte adhesion to vascular endothelial cells by inhibiting expression of adhesion molecules (e.g. CD18) on leukocytes.

U.S. Pat. Nos. 4,992,437 and 5,439,905 disclose thienodiazepine compounds having CCK antagonistic action or gastrin antagonistic action; EP-A 656361 discloses thienotriazolodiazepine compounds having inhibitory effect on cell adhesion; EP-A 638560 discloses a series of thienotriazolodiazepine compounds usable as therapeutic agents for osteoporosis; and EP-A 387613 discloses thienotriazolodiazepine compounds having platelet activating factor (PAF)-inhibitory activity and applicable to ulcerative coliris.

However, the compounds described in various known literatures including the above-mentioned are not sufficient to afford satisfactory inhibitory effect on cell adhesion. Then, the development of a superior agent having a strong inhibitory effect on cell adhesion for the prophylaxis and treatment of rhinitis, dermatitis, asthmatic diseases, inflammatory bowel diseases, nephritis, autoimmune diseases, osteoarthritis, diabetes, malignant tumor, ischemic heart diseases or graft rejection after organ transplantation is desired.

DISCLOSURE OF THE INVENTION

With the aim of searching for a compound (leukocyte adhesion inhibitor) which strongly inhibits expression of VCAM-1 and cell adhesion, in particular, adhesion of leukocytes to vascular endothelial cells, the present inventors have established an assay system for cell adhesion by the use of human umbilical vein-derived endothelial cells (HUVEC) and a human leukemia cell line, and have now found that a novel thienotriazolodiazepine compound which is not specifically exemplified in published documents such as U.S. Pat. No. 5,439,905 has a strong inhibitory effect on cell adhesion.

Accordingly, the present invention provides N-(4-(4-chlorophenyl)-2,3,9-trimethyl-6H-thieno[3,2-f][1,2,4] triazolo- [4,3-a][1,4]diazepin-6-yl)-N'-(2-methoxyphenyl) urea of the formula

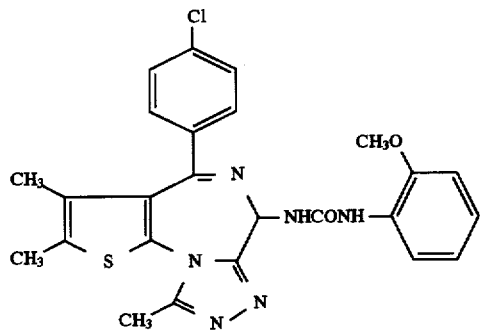

and optical isomers thereof and pharmaceutically acceptable salts thereof.

The optical isomer is selected from: (+)-N-(4-(4-chlorophenyl)-2,3,9-trimethyl-6H-thieno[3,2- f][1,2,4] triazolo[4,3-a][1,4]diazepin-6-yl)-N'-(2-methoxy- phenyl) urea and (−)-N-(4-(4-chlorophenyl)-2,3,9-trimethyl-6H-thieno[3,2- f][1,2,4]triazolo[4,3-a][1,4]diazepin-6-yl)-N'-(2-methoxy- phenyl)urea, and particularly preferred is: (−)-N-(4-(4-chlorophenyl)-2,3,9-trimethyl-6H-thieno[3,2- f][1,2,4]triazolo[4,3-a][1,4]diazepin-6-yl)-N'-(2-methoxy-phenyl)urea.

The present invention also provides methods for prophylaxis or treatment of various diseases in which cell adhesion is involved, comprising administering the compound of formula (1), an optical isomer thereof or a pharmaceutically acceptable salt thereof, and said compounds being specifically used as agents for the prophylaxis or treatment of rhinitis, dermatitis, asthmatic diseases, inflammatory bowel diseases, nephritis, autoimmune diseases, osteoarthritis, diabetes, malignant tumor, ischemic heart disease or graft rejection after organ transplantation.

The present invention also provides pharmaceutical compositions comprising the compound of formula (1), an optical isomer thereof or a pharmaceutically acceptable salt thereof, and a pharmaceutically acceptable additive, which are particularly used in the form of collunarium, inhalant, ointment or cataplasm (poultice) for topical administration.

In the present specification, N-(4-(4-chlorophenyl)-2,3,9-trimethyl-6H-thieno[3,2-f][1,2,4]triazolo[4,3-a][1,4] diazepin- 6-yl)-N'-(2-methoxyphenyl)urea is sometimes referred to as Compound A and (−)-N-(4-(4-chlorophenyl)-2,3,9-trimethyl-6H- thieno[3,2-f][1,2,4]triazolo[4,3-a][1,4] diazepin-6-yl)-N'-(2- methoxyphenyl)urea is sometimes referred to as Compound B.

The pharmaceutically acceptable salts of the compound of formula (1) include addition salts with inorganic acid or organic acid. The hydrates and solvates (e.g. ethanolate) of the compound of formula (1) are also encompassed in the present invention.

The compound of formula (1) can be produced, for example, by condensing a compound of the formula

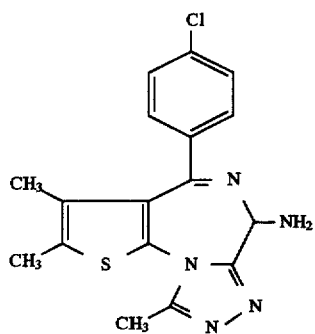

(2)

or a salt thereof, with isocyanate of the formula

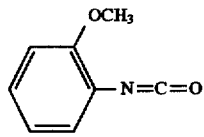

(3)

The condensation reaction of the compound of formula (2) and the compound of formula (3) is carried out in a suitable solvent which does not interfere with the instant reaction. Examples of the solvent include organic solvents such as tetrahydrofuran, diethyl ether, diisopropyl ether, dioxane, dichloromethane, chloroform, ethyl acetate, benzene, toluene, xylene, dimethylformamide and dimethylacetamide.

The temperature of the condensation reaction varies depending on the reagent and solvent to be used. Preferable temperature is generally from −20° C. to the boiling point of the solvent.

The starting compound of formula (2) can be produced by, for example, reacting a compound of the formula

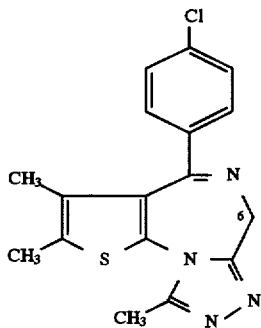

(4)

with a dialkyl carbonate such as diethyl carbonate in the presence of a base such as sodium hydride and potassium tert-butoxide to introduce an alkoxycarbonyl (e.g. ethoxycarbonyl) at the 6-position, reacting the resulting compound with O-(2,4-dinitrophenyl)hydroxylamine to give a compound of the formula

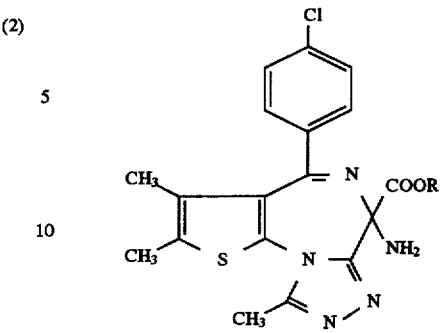

(5)

wherein R is an alkyl such as methyl and ethyl, preferably ethyl, subjecting the compound of formula (5) to hydrolysis in water or a mixed solvent of water and an organic solvent which is preferably methanol, ethanol, diethyl ether, tetrahydrofuran or dioxane, in the presence of a base such as sodium hydroxide, potassium hydroxide and barium hydroxide at a temperature of from about 0° C. to the boiling point of the solvent used, and making the obtained reaction mixture assume acidity using an acid such as hydrochloric acid, hydrobromic acid, hydrofluoric acid, sulfuric acid, trifluoroacetic acid and trifluoro-methanesulfonic acid. The compound of formula (4) can be synthesized by the method described in Japanese Patent Publication No. 43477/1980.

The thus obtained compound of formula (1) can be separated from the reaction mixture and purified by a method known per se such as recrystallization and column chromatography.

The compound of formula (1) can be converted to a salt by treating same with an inorganic acid such as hydrochloric acid, hydrobromic acid, sulfuric acid, phosphoric acid and nitric acid or an organic acid such as camphorsulfonic acid, methanesulfonic acid, benzenesulfonic acid and p-toluenesulfonic acid by a conventional method.

The compound of the present invention is generally obtained as a racemate. The racemate can be resolved into an individual optical isomer by a conventional method such as high performance liquid chromatography (HPLC) using packed optical isomer separation column. Such optical isomer can be also produced by using an optically active starting material.

The inhibitory action of the compound of Example 1 (Compound A) on the expression of VCAM-1 is shown in Experimental Example 1.

EXPERIMENTAL EXAMPLE 1

Inhibitory Effect on Expression of VCAM-1 in Human Umbilical Vein-derived Endothelial Cells (HUVECs)

HUVECs were suspended in 199 medium (Biocell Laboratories, Inc., Rancho Dominguez, Calif. USA) containing 20% fetal calf serum, 20 µg/ml endothelial cell growth factor derived from bovine brain and 100 µg/ml heparin, plated into 96-well microculture plates coated with collagen, and cultured at 37° C. in 5% $CO_2$. When cells were grown to confluence, the cells received tumor necrosis factor-α (100 U/ml) and the test compound A, and cultured for 5 hours. After the cells were washed once with 199 medium, mouse anti-human VCAM-1 monoclonal antibody (2 µg/ml) was added, and the cells were incubated for 1 hour at room temperature. After the cells were washed twice, peroxidase-conjugated anti-mouse immunoglobulin antibody was added, and the cells were incubated for 1 hour at room temperature. After the cells were washed 3 times, a substrate for peroxidase, 2,2'-azino-bis(3-ethylbenzothiazolone-6-sulfonic acid), was added. After the plates were stood for 15 minutes at room temperature, absorbance at 405 nm with a reference wave length of 490 nm was measured with a 96-well microplate reader and was regarded as an indicator of VCAM-1 expression. The results are shown in Table 1.

TABLE 1

| Compound A (pM) | Inhibitory effect (%) on VCAM-1 expression |
| --- | --- |
| 1 | 19.7 |
| 10 | 67.1 |
| 100 | 82.3 |
| 1000 | 80.8 |

As shown in the Table 1, Compound A inhibited expression of VCAM-1 on HUVEC in a concentration-dependent manner, and the $IC_{50}$ thereof was 4.4 pM.

The pharmacological effects of topical administration of Compound A are shown in Experimental Examples 2 to 5.

EXPERIMENTAL EXAMPLE 2

Effect on Oxazolone-induced Ear Edema in Mice

Mice (six per group) were sensitized by applying 50 μl of oxazolone solution (70 mg/ml in acetone) to their shaved abdomen on day 0. On day 7, 5 μl of oxazolone solution was applied to each surface of the right ear. After 24 hours (day 8), the right and left ears were cut out with a puncher of 6 mm in diameter and weighed with an electronic reading balance. The difference in weight between the oxazolone-treated ear (right) and untreated ear (left) was taken to reflect the degree of ear edema. Compound A was dissolved in 20% 2-hydroxypropyl-β-cyclodextrin solution containing 1% dimethyl sulfoxide and injected intradermally into the mouse right ear (25 μl/site) on day 7 (immediately before application of oxazolone). Table 2 shows the result.

TABLE 2

| Treatment | Compound A (μg/site) | Ear edema (right ear-left ear) (mg, mean ± S.D.) | Significance[1] |
| --- | --- | --- | --- |
| Unsensitized | 0 | 7.7 ± 1.6 | Control |
| Unsensitized | 1 | 5.7 ± 1.1 | p < 0.05 |
| Unsensitized | 10 | 5.3 ± 0.7 | p < 0.05 |
| Sensitized | 0 | 16.8 ± 0.7 | Control |
| Sensitized | 1 | 15.0 ± 0.6 | p < 0.01 |
| Sensitized | 10 | 13.3 ± 0.7 | p < 0.01 |

Note:
Compared with control by Dunnett's multiple comparison test.

As shown in Table 2, Compound A inhibited ear edema in sensitized or unsensitized mice in a dose-dependent manner by intradermal administration and this result suggests that Compound A suppressed infiltration of leukocytes into inflammatory site by inhibiting cell adhesion by topical administration.

EXPERIMENTAL EXAMPLE 3

Effect on Picryl Chloride-induced Ear Edema in Mice

Cyclophosphamide (150 mg/kg) was administered subcutaneously to mice on day -2. The mice were sensitized twice by applying 50 μl of picryl chloride solution (70 mg/ml in ethanol) to their shaved abdomen on days 0 and 1. On day 13, 10 μl of picryl chloride solution (10 mg/ml in ethanol) was applied to each surface of the right ear. Two days later (on day 15), the right and left ears were cut out with a puncher of 6 mm in diameter and weighed with an electronic reading balance. The difference in weight between the treated (right) ear and the untreated (left) ear was taken as an indicator of edema. Compound A was dissolved in 20% hydroxypropyl-β-cyclodextrin solution containing 1% dimethyl sulfoxide and injected intradermally into the mouse right ear (25 μl/site). Table 3 shows the result.

TABLE 3

| Cyclo-phosphamide | Sensitization with picryl chloride | Compound A (μl/site) | Ear edema (right ear-left ear) (mg, mean ± S.D.) |
| --- | --- | --- | --- |
| − | − | 0 | 2.4 ± 0.7 |
| + | + | 0 | 10.8 ± 1.3 |
| + | + | 10 | 7.8 ± 0.4 |

The group treated with cyclophosphamide and picryl chloride was taken as a control, and statistical significance was evaluated by Dunnett's test. The data showed the inhibition of picryl chloride-induced mouse ear edema, suggesting that the topical administration of this compound could suppress leukocyte infiltration into inflammatory sites by inhibiting cell adhesion.

EXPERIMENTAL EXAMPLE 4

Effect on Tolylene 2,4-diisocyanate (TDI)-induced Rhinitis in Guinea Pig

Guinea pigs (three to six per group) were sensitized by applying a mixture of TDI and ethyl acetate (1:7) with cotton buds to both of their nasal cavities under anesthetization with diethyl ether on days 0 to 3 and days 7 to 10. On days 27, 29, 31 and 35, the reaction of the guinea pigs was challenged by applying the same mixture to the nasal cavities in a similar manner as described above. Three hours after the last challenge, the guinea pigs were anesthetized with pentobarbital (30 mg/kg, i.p.), and the nasal cavities were washed with physiological saline. Number of leukocytes in the fluid obtained above was counted with an automatic blood cell counter. Compound A (0.1, 1 or 10 μg/20 μl/site×2/guinea pig) was dissolved in 20% hydroxypropyl-β-cyclodextrin solution containing 1% dimethyl sulfoxide and injected into the both nasal cavities of guinea pigs 1 hour before the last challenge (on day 35). Table 4 shows the result.

TABLE 4

| Treatment | Compound A (μg/site) | Number of leukocytes[1] (×100 cells/μl) | Statistical significance[2] |
| --- | --- | --- | --- |
| Unsensitized | 0 | 1.2 ± 0.56 | p < 0.01 |
| Sensitized | 0 | 20.0 ± 2.04 | control |
| Sensitized | 0.1 | 12.7 ± 1.41 | p < 0.01 |
| Sensitized | 1 | 7.1 ± 1.19 | p < 0.01 |
| Sensitized | 10 | 2.8 ± 0.17 | p < 0.01 |

Note:
[1]Mean ± S.D.
[2]Versus control in Dunnett's test

Based on the result of Table 4, it was clarified that the administration of Compound A into the nasal cavity inhibited the leukocyte infiltration in TDI-induced guinea pig rhinitis dose-dependently, and suggested that the topical administration of this compound could suppress the leukocyte infiltration into inflammatory sites by inhibiting cell adhesion.

EXPERIMENTAL EXAMPLE 5

Inhibitory Effect on Topical Eosinotaxis in Lung Induced by Antigen

Test Method

Animal

Male Hartley guinea pigs (4 weeks old, Japan SLC) were bred under the homoiothermal (23±2° C.) and homohumidity (55±5%) conditions.

Preparation of Test Compound Solution

Compound A was dissolved in 20% 2-hydroxypropyl-β-cyclodextrin containing 1% dimethyl sulfoxide to a concentration of 0.01%.

Sensitization and Antigen Challenge

Antigen (egg albumin, Sigma, 10 mg/ml in saline) was nebulized on guinea pigs for 10 minutes with an ultrasonic nebulizer (NE-U12, OMRON CORPORATION). One week later, the antigen was nebulized again in the same manner.

At one week after the second antigen inhalation, mepyramine (Sigma, 10 mg/ml in saline) was intraperitoneally administered by 1 ml/kg. Twenty minutes later, a solution of Compound A (0.01%) or the medium (control) was nebulized for 10 minutes with a jet nebulizer (Nippon Shoji, Ltd.). Immediately thereafter, the antigen (egg albumin, 10 mg/ml) was nebulized for 5 minutes with an ultrasonic nebulizer. Five hours later, the solution of Compound A (0.01%) or the medium was nebulized again for 10 minutes with a jet nebulizer. Unsensitized group did not undergo sensitization or antigen challenge. At 24 hours after the antigen nebulizing, the lung was washed three times with physiological saline (10 ml, 37° C.), and the total number of the cells in the collected lung washings was counted by a colter counter (MEK 4200, Nippon Koden). The lung washings were centrifuged (800 rpm, 10 minutes) and the supernatant was decanted. The remaining cells were suspended in serum and spread on a slide glass. The cells were stained with a slide stainer (Hitachi) and the cells were classified using a microscope (×400). The number of eosinophils was calculated from the ratio of existing cells and the total cell number. The results are shown in Table 5.

TABLE 5

|  | Number of eosinophils (×10$^6$) |
| --- | --- |
| Control | 20.7 ± 2.95 |
| Compound A (0.01%) | 8.9 ± 3.7* |
| Unsensitized group | 4.7 ± 1.46** |

Note:
*p < 0.05
**p < 0.01 vs control group (Dunnett's test)

As shown in Table 5, inhalation of Compound A (0.01%) resulted in significant decrease in eosinophil in lung washings.

The results of Experimental Example 1 clarified that the compound of the present invention strongly inhibits expression of VCAM-1 and is useful as a cell adhesion inhibitor. The results of Experimental Examples 2–5 suggest that the topical administration of the compound of the present invention is effective for dermatitis, rhinitis and asthma.

EXPERIMENTAL EXAMPLE 6

Effect on CD11b Expression in Human Histiocytic Leukemia Cell Line, U937

Effect on the expression of CD11b antigen, which constitutes the a chain of Mac-1, one of the adhesion molecules expressed on the surface of leukocytic cells, was investigated. U937 cells were suspended in RPMI1640 medium containing 20% fetal calf serum, plated with phorbol 12,13-dibutyrate (PDB, 10 ng/ml) and Compound A or Compound B into 96-well filtration plates (30,000 cells/well), and cultured for 3 days at 37° C. in 5% $CO_2$. After the cells were washed once with RPMI1640 medium, rat anti-human CD11b monoclonal antibody (2 μg/ml) was added and the plates were kept for 1 hour on ice. After the cells were washed twice, peroxidase-conjugated anti-rat immunoglobulin antibody (1 μg/ml) was added, and the cells were kept for 1 hour on ice. After the cells were washed 3 times, o-phenylenediamine was added as a substrate for peroxidase. The plates were allowed to stand for 15 minutes at room temperature, and absorbance at 490 nm was measured with a 96-well plate reader. The absorbance was regarded as an indicator of CD11b antigen expression.

Table 6 shows $IC_{50}$ values (μM) obtained by calculating % inhibition when the absorbance in the presence and absence of PDB was taken as 100% and 0%, respectively.

TABLE 6

| | Inhibitory effect on CD11b expression |
| --- | --- |
| Test Compound | ($IC_{50}$, μM) |
| Compound A | 0.25 |
| Compound B | 0.063 |

As shown in Table 6 above, the compounds of the present invention strongly inhibited CD11b expression in U937 cells.

EXPERIMENTAL EXAMPLE 7

Effect on Cell Adhesion of Guinea Pig Peritoneal Cells to Human Umbilical Vein-derived Endothelial Cells (HUVECs)

HUVECs were suspended in 199 medium containing 20% fetal calf serum, 20 μg/ml endothelial cell growth factor derived from bovine brain and 100 μg/ml heparin, plated into 96-well microculture plates coated with collagen, and cultured at 37° C. in 5% $CO_2$. When cells were grown to confluence, interleukin 1 (10 U/ml) was added, and the cells were cultured for 24 hours. After the cells were washed once with 199 medium, leukotriene B4 (1 μM), Compound A and guinea pig peritoneal cells [300,000 cells/well, obtained by intraperitoneally injecting 0.1% oyster glycogen (25 ml) and recovering 5 hours later] were added, and the cells were incubated for 30 minutes at 37° C. in 5% $CO_2$. After nonadherent cells were removed by inverting the plates, rose bengal solution (0.25% in phosphate-buffered physiological saline) was added and the plates were kept still for 5 minutes. The cells were washed twice with 199 medium. Ethanol (50% in phosphate-buffered physiological saline) was added (200 μl/well) and the cells were kept still for 30 minutes to allow the leakage of rose bengal dye incorporated into the cells. Absorbance at 520 nm was measured with a 96-well plate reader and the value obtained by subtracting absorbance of the well Containing HUVECs alone was taken as an indicator of cell adhesion. Table 7 shows the result.

TABLE 7

| Leukotriene B4 (μM) | Compound A (μM) | Cell adhesion (absorbance at 520 nm) | Inhibition (%) |
|---|---|---|---|
| 0 | 0 | 0.074 | 100 |
| 1 | 0 | 0.214 | 0 |
| 1 | 0.01 | 0.222 | −4.7 |
| 1 | 0.1 | 0.169 | 32.6 |
| 1 | 1 | 0.080 | 95.5 |
| 1 | 10 | 0.077 | 97.9 |

As shown in Table 7, Compound A inhibited adhesion of guinea pig peritoneal cells to vascular endothelial cells in a concentration-dependent manner, and the concentration necessary for 50% inhibition ($IC_{50}$ values, μM) was about 0.2 μM.

EXPERIMENTAL EXAMPLE 8

Effect on Oxazolone-induced Ear Edema in Mice

Mice were sensitized by applying 50 μl of oxazolone solution (50 mg/ml in acetone) to their shaved abdomen on day 0. On day 7, 5 μl of oxazolone was applied to each surface of the right ear. After 24 hours, the right and left ears were cut out with a puncher of 6 mm in diameter and weighed with an electronic reading balance. The difference in weight between the treated ear (right) and untreated ear (left) was taken to reflect the degree of ear edema. Compound A was suspended in 0.5% methylcellulose solution and administered orally (0.1 ml/10 g body weight) on days 0 to 8. Table 8 shows the result.

TABLE 8

| Treatment | Compound A (mg/kg/day) | Ear edema (right ear-left ear) (mg, mean ± S.D.) | Significance* |
|---|---|---|---|
| Unsensitized | 0 | 8.2 ± 0.8 | |
| Sensitized | 0 | 17.6 ± 1.1 | Control |
| Sensitized | 10 | 16.0 ± 0.7 | p < 0.01 |
| Sensitized | 30 | 15.4 ± 0.5 | p < 0.01 |
| Sensitized | 100 | 14.4 ± 0.5 | p < 0.01 |

*:by Duncan's new multiple comparison test

As shown in Table 8, Compound A inhibited ear edema in mice in a dose-dependent manner, and this result suggests that Compound A suppressed infiltration of leukocytes into inflammatory sites by inhibiting cell adhesion in vivo.

The above-mentioned experimental results show that the compound of the present invention has inhibitory effect on cell adhesion and is useful as a medicine.

When using the compound of the present invention or a pharmaceutically acceptable salt thereof as a medicine, it is appropriately mixed with a pharmaceutically acceptable carrier, excipient, diluent, solubilizer or stabilizer, and formulated into tablet, capsule, powder, injection or transfusion. It can be also formulated into a pharmaceutical preparation for topical administration, such as collunarium, inhalant, ointment, cataplasm and eye drop.

BEST MODE FOR EMBODYING THE INVENTION

The present invention is explained in more detail in the following Starting Material Preparation Examples, Examples and Formulation Examples. It is needless to say that the present invention is not limited to these Examples.

Starting Material Preparation Example 1

4-Chlorophenyl cyanomethyl ketone, morpholine and ethyl methyl ketone were dissolved in ethanol, and sulfur was suspended. The suspension was refluxed under heating for 10 hours. After completion of the reaction, the solvent was distilled away under reduced pressure, and the residue was dissolved in chloroform. The mixture was washed with water, and dried over anhydrous magnesium sulfate. Chloroacetyl chloride was added dropwise, and the mixture was refluxed under heat for 1 hour. After completion of the reaction, the resulting mixture was washed with a saturated aqueous solution of sodium hydrogencarbonate and dried over anhydrous magnesium sulfate, and the solvent was distilled away under reduced pressure. Methanol was added to the residue and crystallized to give N-(2-(3-(4-chlorobenzoyl)-4,5-dimethyl)thienyl) chloroacetamide. This compound was dissolved in tetrahydrofuran, and sodium iodide was suspended therein. The suspension was refluxed under heat for 2 hours. The reaction mixture was cooled to −50° C. with dry ice-acetone, and liquid ammonia was added, follwed by stirring. After completion of the reaction, the solvent was distilled away under reduced pressure, and the residue was dissolved in ethyl acetate. After washing with water, the mixture was dried over anhydrous magnesium sulfate, and the solvent was distilled away under reduced pressure. The residue was dissolved in isopropyl alcohol, and acetic acid was added. The mixture was refluxed under heat for 5 hours. The solvent was distilled away under reduced pressure, and the residue was dissolved in chloroform. The mixture was washed with a saturated aqueous solution of sodium hydrogencarbonate, and dried over anhydrous magnesium sulfate. The solvent was distilled away under reduced pressure, and crystallization from ethyl acetate affords 5-(4-chlorophenyl)-6,7-dimethyl-1,2-dihydro-3H-thieno[2,3- e][1,4]diazepin-2-one.

5-(4-Chlorophenyl)-6,7-dimethyl-1,2-dihydro-3H-thieno[2,3- e][1,4]diazepin-2-one was dissolved in chloroform, and diphosphorus pentasulfide was added with stirring. The mixture was refluxed under heat for 3 hours. After completion of the reaction, the reaction mixture was neutralized with a saturated aqueous solution of sodium hydrogencarbonate, washed with water and dried over anhydrous magnesium sulfate. The solvent was distilled away under reduced pressure, and the residue was suspended in methanol. To the suspension was added 100% hydrazine hydrate under cooling, and the mixture was stirred at room temperature for 2 hours. After completion of the reaction, precipitated crystals were collected by filtration to give 5-(4-chlorophenyl)-6,7-dimethyl-1,2-dihydro- 3H-thieno[2, 3-e][1,4]diazepine-2-hydrazone, melting point 226° C. (decomposition). This compound was suspended in toluene, and triethyl orthoacetate was added. The mixture was stirred at 80° C. for 4 hours. After completion of the reaction, the solvent was distilled away under reduced pressure, and obtained crude crystals were recrystallized from ethyl acetate to give 4-(4-chlorophenyl)-2,3,9-trimethyl-6H-thieno[3,2-f][1,2,4]- triazolo[4,3-a][1,4]diazepine, melting point not less than 250° C. $^1$H—NMR ($CDCl_3$, ppm) δ:1.64 (s,3H), 2.39 (s,3H), 2.63 (s,3H), 4.06 (d,1HJ=12Hz), 5.06 (d,1HJ=12Hz), 7.22–7.44 (m,4H)

Starting Material Preparation Example 2

4-(4-Chlorophenyl)-2,3,9-trimethyl-6H-thieno[3,2- f][1,2,4]triazolo[4,3-a][1,4]diazepine (12 g) and sodium hydride (2.4 g) were added to diethyl carbonate (150 ml), and the mixture was heated. Bubbling of hydrogen gas began at about 100° C. and the color of the reaction mixture gradually changed to purple. After refluxing for an hour, the reaction mixture was cooled to 20° C., added with O-(2,4-dinitrophenyl)hydroxylamine (8 g), and stirred for 2 hours. After the reaction, the reaction mixture was poured into ice water and a diethyl carbonate layer was separated. The layer was washed twice with water and dried over anhydrous magnesium sulfate. Diethyl carbonate was distilled away under reduced pressure and diisopropyl ether was added to the obtained residue. The precipitated crystals were filtrated to give 11 g of ethyl (6-amino-4-(4-chlorophenyl)- 2,3,9-trimethyl-6H-thieno[3,2-f][1,2,4]triazolo[4,3- a][1,4] diazepin-6-yl)carboxylate.

Ethyl (6-amino-4-(4-chlorophenyl)-2,3,9-trimethyl-6H-thieno[3,2-f][1,2,4]triazolo[4,3-a][1,4]diazepin-6-yl)- carboxylate (11 g) was dissolved in a mixed solution of ethanol (250 ml) and water (80 ml). Barium hydroxide octahydrate (8.4 g) was added and the mixture was stirred at room temperature for 24 hours. The solvent was distilled away under reduced pressure, and water (100 ml) was added. The pH of the mixture was adjusted to 2 with 1N hydrochloric acid and stirred for 20 minutes. The mixture was neutralized with an aqueous solution of sodium hydrogencarbonate and extracted twice with chloroform. The organic layer was dried over anhydrous magnesium sulfate. The solvent was distilled away under reduced pressure and the residue was subjected to silica gel column chromatography. The solvent was distilled away, the resulting residue was crystallized from diisopropyl ether, and the crystals were filtrated to give 7 g of 6-amino-4-(4-chlorophenyl)-2,3,9- trimethyl-6H-thieno[3,2-f][1,2,4]triazolo[4,3-a][1,4]diazepine, melting point 192°–197° C. with decomposition.

Example 1

6-Amino-4-(4-chlorophenyl)-2,3,9-trimethyl-6H-thieno [3,2- f][1,2,4]triazolo[4,3-a][1,4]diazepine (4 g) was dissolved in chloroform (30 ml). 2-Methoxyphenyl isocyanate (1.7 ml) was added, and the mixture was stirred for 30 minutes. The reaction mixture was subjected to silica gel column chromatography, and the resultant crystals were recrystallized from ethanol to give 5.14 g of N-(4-(4-chlorophenyl)-2,3,9- trimethyl-6H-thieno[3,2-f][1,2,4]triazolo[4,3-a][1,4]diazepin- 6-yl)-N'-(2-methoxyphenyl) urea, melting point 261°–262° C.

Example 2

N-(4-(4-Chlorophenyl)-2,3,9-trimethyl-6H-thieno[3,2-f]-[1,2,4]triazolo[4,3-a][1,4]diazepin-6-yl)-N'-(2-methoxyphenyl)- urea (200 mg) obtained in Example 1 was subjected to the separation by HPLC using an optical isomer separating column (Chirasphar®, Merck, inner diameter 25 mm, length 250 mm) with a mixed solution of n-hexane:dioxane:isopropyl alcohol (volume ratio 1800:1200:45) as a mobile phase at a flow rate of 10 ml/minute. The fractions eluted out 40 minutes later were combined and concentrated under reduced pressure to give 53 mg of (+)-N-(4-(4-chlorophenyl)-2,3,9-trimethyl-6H-thieno[3,2- f][1,2,4]triazolo[4,3-a][1,4]diazepin-6-yl)-N'-(2-methoxy- phenyl)urea as a white amorphous powder. $[\alpha]_D^{24}=+33.2°$ (c=0.82, methanol)

Then, the fractions eluted out 45 minutes later were concentrated under reduced pressure to give 60 mg of (−)-N-(4- (4-chlorophenyl)-2,3,9-trimethyl-6H-thieno[3,2-f][1,2,4]- triazolo[4,3-a][1,4]diazepin-6-yl)-N'-(2-methoxyphenyl)urea as a white amorphous powder. $[\alpha]_D^{23}=$ −37.4° (c=0.6, methanol)

The formulation examples of the compound of Example 1 (Compound A) are given in the following.

Formulation Example 1

Compound A (0.5 part by weight, hereinafter the same), lactose (25 parts), crystalline cellulose (35 parts) and corn starch (3 parts) are thoroughly mixed, and the mixture is kneaded well with a binder prepared from 2 parts of corn starch. The kneaded mixture is passed through a 16 mesh sieve, dried in an oven at 50° C. and passed through a 24 mesh sieve. The thus-obtained kneaded powder is mixed well with corn starch (8 parts), crystalline cellulose (11 parts) and talc (9 parts), and compressed with pressure to give tablets containing 0.5 mg of the active ingredient per tablet.

Formulation Example 2

Compound A (1.0 mg) and sodium chloride (9.0. mg) are dissolved in an injectable water and filtered to remove pyrogen. The filtrate is aseptically placed in an ampoule, sterilized and melt-sealed to give an injection containing 1.0 mg of the active ingredient.

Formulation Example 3

Polyacrylic acid is completely dissolved with swelling in water and a solution of sodium hydroxide is added in an appropriate amount to allow gelling. The concentration of polyacrylic acid in the gel is 0.01–2% w/v and pH is 4–8. Compound A is added to the gel with stirring to a concentration of 0.1% w/v, whereby a collunarium of Compound A is obtained.

Formulation Example 4

Compound A is finely pulverized in a jet mill. Inhalation grade lactose (9 parts by weight) is added to part by weight of the finely pulverized Compound A and mixed by passing through a sieve and using a shaker mixer for 30 minutes. The mixture is packed in an inhaler, whereby a powder inhalant is obtained.

Formulation Example 5

An ointment of Compound A is prepared using the following ingredients.

|  | weight/weight % |
|---|---|
| Compound A | 0.1 |
| White soft paraffin | 49 |
| Cetyl alcohol | 10 |
| White beeswax | 5 |
| Sorbitan sesquioleate | 5 |
| Lauromacrogol | 0.5 |
| Methyl p-hydroxybenzoate | 0.1 |
| Propyl p-hydroxybenzoate | 0.1 |
| Purified water | amount to make the total 100% |

INDUSTRIAL APPLICABILITY

The compounds of the present invention strongly and selectively inhibit expression of VCAM-1 and have an inhibitory effect on leukocyte adhesion to vascular endothelial cells, thus suggesting their usefulness as cell adhesion inhibitors. Accordingly, the compounds of the present invention can be used for prophylaxis or treatment of various diseases in which cell adhesion is involved in the onset and progress thereof, such as rhinitis (e.g. allergic rhinitis and pollinosis), dermatitis (e.g. contact dermatitis and atopic dermatitis), asthmatic diseases including chronic bronchial asthma, inflammatory bowel diseases (e.g. Crohn's disease and ulcerative colitis), nephritis including glomerular nephritis, autoimmune diseases (e.g. rheumatoid arthritis and systemic lupus erythematosus), osteoarthritis, diabetes, malignant tumor and ischemic heart diseases, and graft rejection after organ transplantation.

What is claimed is:

1. N-(4-(4-chlorophenyl)-2,3,9-trimethyl-6H-thieno [3,2-f][1,2,4]triazolo[4,3-a][1,4]diazepin-6-yl)-N'-(2- methoxyphenyl)urea, an optical isomer thereof or a pharmaceutically acceptable salt thereof.

2. The compound of claim 1, wherein the optical isomer is (−)-N-(4-(4-chlorophenyl)-2,3,9-trimethyl-6H-thieno[3,2-f][1,2,4]-triazolo[4,3-a][1,4]diazepin-6-yl)-N'-(2-methoxyphenyl)urea, or a pharmaceutically acceptable salt thereof.

3. A pharmaceutical composition comprising N-(4-(4-chlorophenyl)-2,3,9-trimethyl-6H-thieno[3,2-f][1,2,4]triazolo[4,3-a]-[1,4]diazepin-6-yl)-N'-(2-methoxyphenyl)urea, an optical isomer thereof or a pharmaceutically acceptable salt thereof, and an additive for pharmaceuticals.

4. The pharmaceutical composition of claim 3, which is in the form of a collunarium.

5. The pharmaceutical composition of claim 3, which is in the form of an inhalant.

6. The pharmaceutical composition of claim 3, which is in the form of an ointment.

7. The pharmaceutical composition of claim 3, which is in the form of a cataplasm.

8. A method for inhibiting VCAM-1 expression in a human, comprising administering N-(4-(4-chlorophenyl)-2,3,9-trimethyl-6H-thieno[3,2-f][1,2,4]triazolo[4,3-a][1,4]diazepin-6-yl)-N'-(2-methoxyphenyl)urea, an optical isomer thereof or a pharmaceutically acceptable salt thereof.

9. The method of claim 8, wherein said N-(4-(4-chlorophenyl)-2,3,9-trimethyl-6H-thieno[3,2-f][1,2,4]triazolo[4,3-a][1,4]diazepin-6-yl)-N'-(2-methoxyphenyl)urea, optical isomer thereof or pharmaceutically acceptable salt thereof, is administered topically.

10. A method for the prophylaxis or treatment of rhinitis in a human, comprising administering N-(4-(4-chlorophenyl)-2,3,9-trimethyl-6H-thieno[3,2-f][1,2,4]triazolo[4,3-a][1,4]diazepin-6-yl)-N'-(2-methoxyphenyl)urea, an optical isomer thereof or a pharmaceutically acceptable salt thereof.

11. A method for the prophylaxis or treatment of dermatitis in a human, comprising administering N-(4-(4-chlorophenyl)-2,3,9-trimethyl-6H-thieno[3,2-f][1,2,4]triazolo[4,3-a][1,4]diazepin-6-yl)-N'-(2-methoxyphenyl)urea, an optical isomer thereof or a pharmaceutically acceptable salt thereof.

12. A method for the prophylaxis or treatment of asthma in a human, comprising administering N-(4-(4-chlorophenyl)-2,3,9-trimethyl-6H-thieno[3,2-f][1,2,4]triazolo[4,3-a][1,4]diazepin-6-yl)-N'-(2-methoxyphenyl)urea, an optical isomer thereof or a pharmaceutically acceptable salt thereof.

* * * * *